(12) United States Patent
Lee

(10) Patent No.: US 9,353,409 B2
(45) Date of Patent: May 31, 2016

(54) COMPOSITIONS AND METHODS FOR RT-PCR

(71) Applicant: Jun Euihum Lee, San Diego, CA (US)

(72) Inventor: Jun Euihum Lee, San Diego, CA (US)

( * ) Notice: Subject to any disclaimer, the term of this patent is extended or adjusted under 35 U.S.C. 154(b) by 0 days.

(21) Appl. No.: 13/871,841

(22) Filed: Apr. 26, 2013

(65) Prior Publication Data

US 2014/0199699 A1    Jul. 17, 2014

Related U.S. Application Data

(60) Provisional application No. 61/752,639, filed on Jan. 15, 2013.

(51) Int. Cl.
*C12P 19/34*    (2006.01)
*C12Q 1/68*    (2006.01)

(52) U.S. Cl.
CPC .............. *C12Q 1/686* (2013.01); *C12Q 1/6806* (2013.01)

(58) Field of Classification Search
CPC .................. C12Q 2527/125; C12Q 2527/137; C12Q 1/6806; C12Q 1/686; C12Q 2531/113
USPC ....................................................... 435/91.2
See application file for complete search history.

(56) References Cited

U.S. PATENT DOCUMENTS

2004/0209276 A1* 10/2004 Smith et al. ........................ 435/6
2011/0195460 A1* 8/2011 Getts et al. ................... 435/91.3

OTHER PUBLICATIONS

USB Cororation., https://www.gelifesciences.com/gehcl_images/GELS/Related%20content/Files/1314787424814/litdocFideliTaq_RTPCR_MasterMix_20110831124727.pdf, May 2004, pp. 1-19.*
Norgen Biotek Corporation., https://norgenbiotek.com/display-product-pcr-master-mix.php?ID=235, 2X RT-PCR Master Mix with Dual Dye, Product information, 2010, pp. 1-4.*
Qu et al., PLOS, vol. 4, issue 3, pp. e629 1-7, Mar. 2010.*
Piche et al., Journal of Biomolecular Techniques, vol. 16, issue 3, pp. 239-247, Sep. 2005.*
Tomlinson et al., Applied and Environmental Microbiology, vol. 71, No. 11, pp. 6702-6710, Nov. 2005.*
Carninci et al., PNAS, vol. 95, pp. 520-524, Jan. 1998.*

* cited by examiner

*Primary Examiner* — Cynthia B Wilder
(74) *Attorney, Agent, or Firm* — East West Law Group; Heedong Chae

(57) ABSTRACT

The present invention relates to methods and compositions having trehalose and DNA polymerase for facilitating the rapid and efficient amplification of nucleic acid molecules and the detection and quantitation of RNA molecules, and for increasing the detection sensitivity and reliability through generation of secure cDNA molecules prior to gene-specific primer dependent amplification. The reagent mixture comprises a ready to use reagent solution, wherein the solution comprises: (a) trehalose in a concentration between about 5% and about 35%; (b) a viral reverse transcriptase; and (c) at least one DNA polymerases, in a buffer suitable for use in a reverse transcription reaction, wherein the buffer comprises a co-factor metal ion and nucleoside triphosphates.

18 Claims, 3 Drawing Sheets

FIG. 1: Freeze-thaw stability
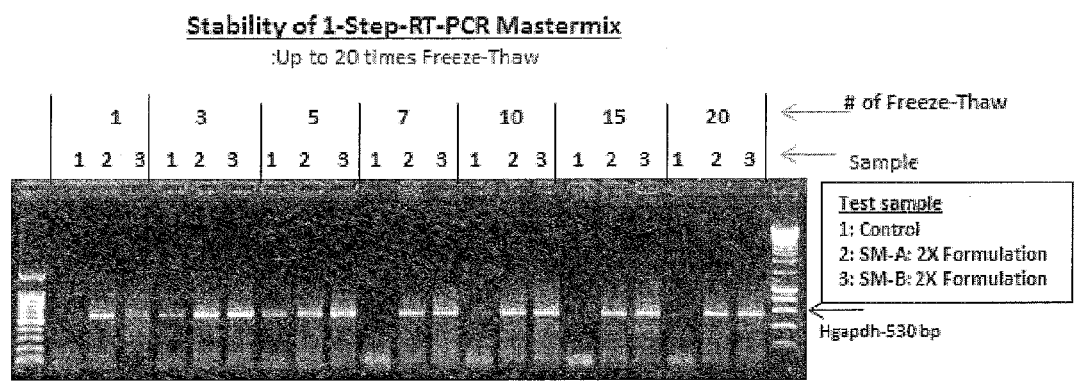

FIG. 2: Real time storage stability
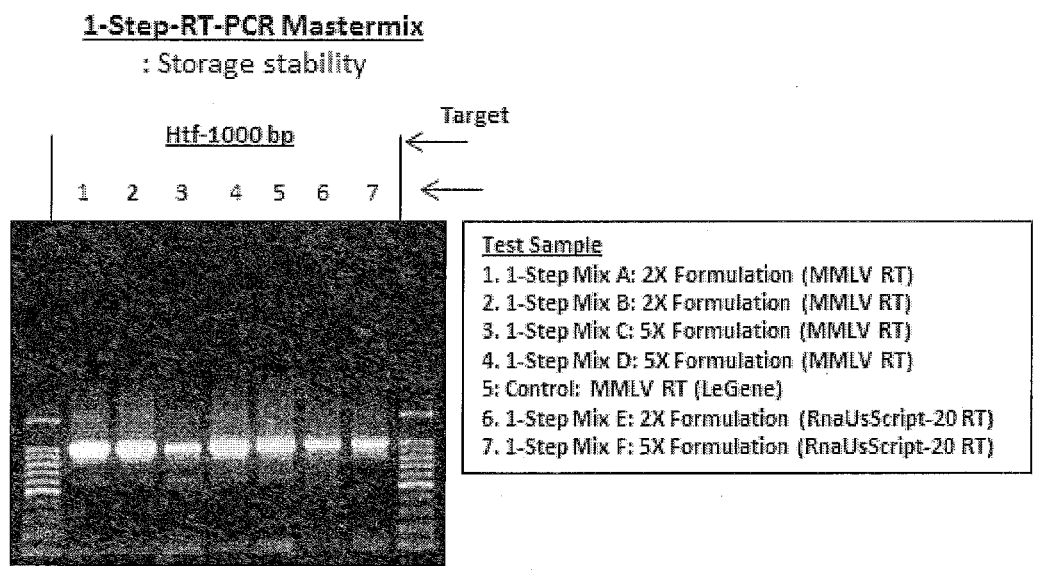

FIG. 3: 1-Step RT-PCR with 2X and 5X RT-PCR mastermixes
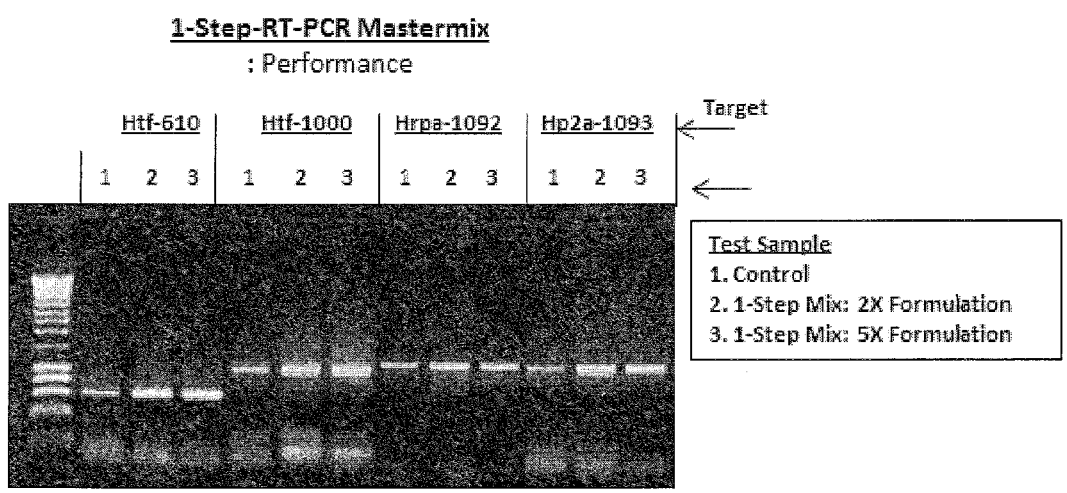

COMPOSITIONS AND METHODS FOR RT-PCR

CROSS REFERENCE TO RELATED APPLICATIONS

This application claims priority to Provisional Application Ser. No. 61/752,639, filed Jan. 15, 2013, the contents of which are incorporated herein by reference in their entirety.

FIELD

The present invention provides methods and compositions for preparing RT-PCR, and more specifically, compositions having trehalose and DNA polymerase for facilitating the rapid and efficient amplification of nucleic acid molecules and the detection and quantitation of RNA molecules, and for increasing the detection sensitivity and reliability through generation of secure cDNA molecules prior to gene-specific primer dependent amplification.

BACKGROUND

The genetic framework of an organism is encoded in the double-stranded sequence of nucleotide bases in the deoxyribonucleic acid (DNA) and the genetic content of a particular segment of DNA, or gene, is manifested only upon production of the protein encoded by the gene. To produce a protein, one strand of the DNA is copied to produce a specific sequence of ribonucleic acid (RNA) and this particular type of RNA is called messenger RNA (mRNA).

Within a given cell, tissue or organism, there exist many mRNA species, each encoding a separate and specific protein, and the identity and levels of specific mRNAs present in a particular sample provides clues to the biology of the particular tissue or sample being studied. Therefore, the detection, analysis, transcription, and amplification of RNAs are among the most important procedures in modern molecular biology.

A common approach to the study of gene expression is the production of complementary DNA (cDNA). In this technique, the mRNA molecules from an organism are isolated from an extract of the cells or tissues of the organism. From these purified mRNA molecules, cDNA copies may be made using the enzyme reverse transcriptase (RT), which results in the production of single-stranded cDNA molecules. The term "reverse transcriptase" describes a class of polymerases characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation.

Avian myoblastosis virus (AMV) reverse transcriptase was the first widely used RNA-dependent DNA polymerase (Verma, Biochim. Biophys. Acta 473:1 (1977)). The enzyme has 5'-3' RNA-directed DNA polymerase activity, 5'-3' DNA-directed DNA polymerase activity, and RNase H activity. RNase H is a processive 5' and 3' ribonuclease specific for the RNA strand for RNA-DNA hybrids (Perbal, A Practical Guide to Molecular Cloning, New York: Wiley & Sons (1984)). Errors in transcription cannot be corrected by reverse transcriptase because known viral reverse transcriptases lack the 3'.fwdarw.5' exonuclease activity necessary for proofreading (Saunders and Saunders, Microbial Genetics Applied to Biotechnology, London: Croom Helm (1987)). A detailed study of the activity of AMV reverse transcriptase and its associated RNase H activity has been presented by Berger, et al., Biochemistry 22:2365-72 (1983).

Another reverse transcriptase which is used extensively in molecular biology is reverse transcriptase originating from Moloney murine leukemia virus (M-MLV). See, e.g., Gerard, G. R., DNA 5:271-279 (1986) and Kotewicz, M. L., et al., Gene 35:249-58 (1985). M-MLV reverse transcriptase substantially lacking in RNase H activity has also been described. See, e.g., U.S. Pat. No. 5,244,797.

One of the most widely used techniques to study gene expression exploits first-strand cDNA for mRNA sequence(s) as template for amplification by the polymerase chain reaction, PCR. This method, often referred to as RNA PCR or reverse transcriptase PCR (RT-PCR), exploits the high sensitivity and specificity of the PCR process and is widely used for detection and quantification of RNA. Recently, the ability to measure the kinetics of a PCR reaction by on-line detection in combination with these RT-PCR techniques has enabled accurate and precise measurement of RNA sequences with high sensitivity. This has become possible by detecting the RT-PCR product through fluorescence monitoring and measurement of PCR product during the amplification process by fluorescent dual-labeled hybridization probe technologies, such as the "TaqMan" 5' fluorogenic nuclease assay described by Holland, et al. (Proc. Natl. Acad. Sci. U.S.A. 88, 7276 (1991)), and Gibson, et al. (Genome Res. 6, 99 (1996) or "Molecular Beacons" (Tyagi, S. and Kramer, F. R. Nature Biotechnology 14, 303 (1996)) has described use of dual-labeled hairpin primers. One of the more widely used methods is the addition of double-strand DNA-specific fluorescent dyes to the reaction such as SYBR Green I (Wittwer, et al., Biotechniques 22, 130 (1997). These improvements in the PCR method have enabled simultaneous amplification and homogeneous detection of the amplified nucleic acid without purification of PCR product or separation by gel electrophoresis. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR, also referred to as quantitative PCR, or qPCR. The general principles for template quantification by real-time PCR were first disclosed by Higuchi R, G Dollinger, P S Walsh and R. Griffith. Use of real time PCR methods provides a significant improvement towards this goal. However, real-time PCR quantification of mRNA is still bounded by limitations of the process of reverse transcription.

To attempt to address the technical problems often associated with RT-PCR, a number of protocols have been developed taking into account the three basic steps of the procedure: (a) the denaturation of RNA and the hybridization of reverse primer; (b) the synthesis of cDNA; and (c) PCR amplification. In the so-called "uncoupled" RT-PCR procedure (e.g., two-step RT-PCR), reverse transcription is performed as an independent step using the optimal buffer condition for reverse transcriptase activity. Following cDNA synthesis, the reaction is diluted to decrease $MgCl_2$ and deoxyribonucleoside triphosphate (dNTP) concentrations to conditions optimal for Taq DNA Polymerase activity, and PCR is carried out according to standard conditions (see U.S. Pat. Nos. 4,683,195 and 4,683,202). By contrast, "coupled" RT-PCR methods use a common or compromised buffer for reverse transcriptase and Taq DNA Polymerase activities. In one version, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of $Mn^{++}$, then PCR is carried out in the presence of $Mg^{++}$ after the removal of $Mn^{++}$ by a chelating agent. Finally, the "continuous" method (e.g., one-step RT-PCR) integrates the three RT-PCR steps into a single continuous reaction that avoids the opening of the reaction tube for component or enzyme addition. Continuous RT-PCR has been described as a single enzyme system using the reverse transcriptase activity of thermostable Taq DNA Polymerase and Tth polymerase and as a two-enzyme system using AMV-RT and Taq DNA Polymerase wherein the initial 65 degree. RNA denaturation step was omitted.

Attempts to streamline the process of RT-PCR have not been easy, and several reports have documented an interference between reverse transcriptase and thermostable DNA polymerase Taq when used in combination in a single tube RT-PCR resulting in low sensitivity or lack of results. For example, there has been at least one report of a general inhibition of Taq DNA polymerase when mixed with reverse transcriptases in one-step/one tube RT-PCR mixtures (Sellner, L. N., et al., Nucl. Acids Res. 20(7):1487-90 (1992)). This same report indicated that the inhibition was not limited to one type of RT: both AMV-RT and M-MLV-RT inhibited Taq DNA polymerase and limited the sensitivity of RT-PCR. Under the reaction conditions used in the Sellner, et al. Other reports describe attempts to develop conditions for one-step RT-PCR reactions. For example, the use of AMV-RT for one-step RT-PCR in a buffer comprising 10 mM Tris-HCl, (pH 8.3), 50 mM KCl, 1.5 mM MgCl.sub.2, and 0.01% gelatin has been reported (Aatsinki, J. T., et al., BioTechniques 16(2):282-88 (1994)), while another report demonstrated one-step RT-PCR using a composition comprising AMV-RT and Taq DNA polymerase in a buffer consisting of 10 mM Tris-HCl, pH 8.3, 50 mM KCl, 0.01% gelatin and 1.5 mM $MgCl_2$ (Mallet, F., et al., BioTechniques 18(4):678-87 (1995)). Under the reaction conditions used in the latter report, substitution of M-MLV-RT (RNase H.sup.+ or RNase H.sup.- forms) for AMV-RT showed the same activity in the continuous RT-PCR reaction.

One-step RT-PCR provides several advantages over uncoupled RT-PCR. One-step RT-PCR requires less handling of the reaction mixture reagents and nucleic acid products than uncoupled RT-PCR (e.g., opening of the reaction tube for component or enzyme addition in between the two reaction steps), and is therefore less labor intensive, reducing the required number of person hours. One-step RT-PCR also requires smaller sample, and reduces the risk of contamination (Sellner and Turbett, 1998). The sensitivity and specificity of one-step RT-PCR has proven well suited for studying expression levels of one to several genes in a given sample or the detection of pathogen RNA.

In contrast, use of non-specific primer in the "uncoupled" RT-PCR procedure provides opportunity to capture all RNA sequences in a sample into first-strand cDNA, thus enabling the profiling and quantitative measurement of many different sequences in a sample, each by a separate PCR. The ability to increase the total amount of cDNA produced, and more particularly to produce cDNA that truly represents the mRNA population of the sample would provide a significant advance in study of gene expression. Specifically, such advances would greatly improve the probability of identifying genes which are responsible for disease in various tissues.

Accordingly, a need for compositions for facilitating the rapid and efficient amplification of nucleic acid molecules and the detection and quantitation of RNA molecules and for increasing the detection sensitivity and reliability through generation of secure cDNA molecules prior to gene-specific primer dependent amplification has been present for a long time. This invention is directed to solve these problems and satisfy a long-felt need.

SUMMARY OF THE INVENTION

The present invention contrives to solve the disadvantages of the prior art. The present invention provides compositions having trehalose in a concentration between about 5% and 35% and at least one DNA polymerase for facilitating the rapid and efficient amplification of nucleic acid molecules and the detection and quantitation of RNA molecules, and for increasing the detection sensitivity and reliability through generation of secure cDNA molecules prior to gene-specific primer dependent amplification.

The present invention relates to methods for amplification of nucleic acid molecules by RT-PCR and kits for making RT-PCR molecules. Specifically, the invention provides compositions and methods for the amplification of nucleic acid molecules in a simplified PCR amplification procedure using combinations of reverse transcriptase and thermostable DNA polymerase enzymes in conjunction mixture of primers with gene-specific primers. The compositions according to the present invention also comprise mixtures of reagents, including reverse transcriptases, DNA polymerases, thermostable DNA polymerases, buffers, cofactors and other components, suitable for immediate use in conversion of RNA into RT-PCR molecules without dilution or addition of further components. These compositions are useful, alone or in the form of kits, for nucleic acid amplification or for any procedure utilizing RT-PCR in a variety of research, medical, diagnostic, forensic and agricultural applications. The invention also is useful in the rapid production and amplification of cDNAs which may be used for a variety of applications. Besides, the invention facilitates the rapid and efficient amplification of nucleic acid molecules and the detection and quantitation of RNA molecules.

The invention also provides improved methods of amplifying nucleic acid molecules from mRNA templates under conditions sufficient to increase the detection sensitivity and reliability through generation of secure cDNA molecules prior to gene-specific primer dependent amplification. Specifically, the invention relates to the use of oligo-dT or random primer or a mixture of oligo(dT) primer and random primer in a first-strand cDNA synthesis reaction. The invention also may comprise no random primer and oligo-dT depending on application purpose.

In one aspect of the invention, the buffer may comprise a monovalent cation selected from the group consisting of Na and K, a magnesium salt, a reducing agent, nucleoside triphosphates, and at least one non-ionic detergent. The buffer may further comprise at least one primer suitable for priming reverse transcription of a template by the reverse transcriptase. The mixture may also comprise an RNase inhibitor protein. In one embodiment, the buffer comprises a potassium salt, a magnesium salt, nucleoside triphosphates, DTT, at least one or more reverse transcriptases, at least one or more DNA polymerases, at least one non-ionic detergent, BSA, and an RNase inhibitor protein.

In any of these methods and compositions, two or more reverse transcriptases and two or more DNA polymerases may be used, including any reverse transcriptase as described above.

The advantages of the present invention include that (1) the present invention has facilitated the rapid and efficient amplification of nucleic acid molecules and the detection and quantitation of RNA molecules; (2) The invention has provided improved methods of amplifying nucleic acid molecules from an mRNA templates under conditions sufficient to increase the detection sensitivity and reliability through generation of secure cDNA molecules prior to gene-specific primer dependent amplification; (3) the use of trehalose in a concentration between about 5% and about 35% has increased stability of the RT enzyme that is present in the mixture; (4) in the present invention, some or all of the components of the RT-PCR reaction have become successfully combined and stored as a convenient ready-to-use mix that is stable to prolonged storage at −20° C. and that can simply be added to a nucleic acid template solution and gene specific primers (GSP) when needed; and (5) the present invention has provided a more efficient and uniform priming for cDNA synthesis, resulting in more efficient and representative conversion of mRNA sequences into cDNA regardless of distance from 3' end of mRNA.

Although the present invention is briefly summarized, the fuller understanding of the invention can be obtained by the following drawings, detailed description and appended claims. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 shows stability information for various reaction mixtures, including mastermixes according to the present invention, for use in reverse transcription reactions;

FIG. 2 shows the results and the efficacy of cDNA synthesis with the mastermixes according to the present invention compared to the reagents stored separately under the conditions recommended in the literature; and FIG. 3 shows one-step RT-PCT with 2× and 5× RT-PCR mastermixes according to the present invention.

DETAILED DESCRIPTION OF THE INVENTION

The present invention relates to methods of increasing the efficiency of nucleic acid amplification, particularly, to increasing the sensitivity, accuracy, and reliability of gene expression analysis and quantitation. Thus, the present invention provides improved mRNA detection useful in gene discovery, genomic research, diagnostics and Identification of differentially expressed genes and identification of genes of importance to disease. Other embodiments of the invention relate to stabilized and simplified easy-of-use mastermix solution to improve the reliability of RT-PCR performance.

Use of Primer Combinations

The present invention provides a more efficient, non-bias, and secure priming for cDNA Synthesis prior to gene-specific PCR amplification. The use of optimal concentration and combinations of random primers (GSP) and oligo dT provides an efficient and representative conversion of mRNA sequences into cDNA in advance of GSP amplification. The length of oligo dT can vary from 6 bases to 25 bases and the random primers used according to the present invention (e.g., hexameric, heptameric, octameric, etc.) can vary in size from 6 bases to 9 bases. The amount of random primers can vary from 10 ng to 200 ng for each reaction (20 uL) and that of oligo dT can vary from 2 nM to 50 nM. Alternatively, the invention may comprise no random primer and no oligo dT depending on application purposes.

Convenient and Stable Reagent Compositions

Another embodiment of the present invention is the form in which the reaction mixture is prepared and stably maintained. Traditionally, RT-PCR system components have been supplied as a number of separate components that are assembled into a complete reaction mix just prior to start of RT-PCR reaction primarily due to storage stability issue. A typical kit for RT-PCR contains the following components:
Reaction Buffer (20-80 mM TrisCl pH 8.4, (or 50-100 mM Tris-SO4 pH 8.9),
50-100 mM KCl. d. 1-2 mM $MgCl_2$),
0.2 mM dNTPs,
2-20 units MMLV RT,
1-5 unit Taq DNA polymerase, and
stabilizer.

Each of the above components is provided separately and frozen at −20° C. for storage. The general belief has been that the components cannot be mixed for long term storage. A key component of these systems is reverse transcriptase that is always stored in special storage buffer with at least 50% glycerol, and is only added to the reaction mix immediately prior to start of RT-PCR reaction. For this reason, there has been no existing report of successful formulation of complete mastermix of RT-PCR except thermostable Tth DNA polymerase based RT-PCR. However, unlike the case of viral reverse transcriptases, Tth DNA polymerase is known to be have very weak RT activity in the presence of $Mn^{++}$ and can be for limited application only.

For the first time, we have found that some or all of the components of the RT-PCR reaction can be combined and stored as a convenient ready-to-use mix that is stable to prolonged storage at −20° C. and that can simply be added to a nucleic acid template solution and GSP when needed. The ready to use reaction mixture may contain between about 5% and 35% trehalose to maintain stability of the RT enzyme(s) and DNA polymerases that is present in the mix.

Conventionally, glycerol has been used as an enzyme stabilizer and employed for storage of enzymes. While glycerol based cDNA mixture is not freezing at about −20° C., trehalose based formulation is freezing at about −20° C. and has not been considered as an alternative for storage of enzymes due to the concern on stability issue. However, it has been found in the present invention that trehalose based cDNA can be highly stable under repeated freeze-thaw cycle as shown in FIG. 1.

Various format of RT-PCR mastermix can be successfully formulated (1× format to 10× format) for a variety of applications. The minimum components that may usefully be provided for the mixture are the trehalose, the RT, DNA polymerase, and a suitable buffer component. Suitable buffer compounds, such as Tris-HCl, Tris-$SO_4$, HEPES, etc, are well known in the art. Metal ions necessary for RT and DNA polymerase activity, such as Mg and a monovalent cation such as K, Na may be present in concentrations that are suitable for RT and DNA polymerase activity upon addition to a template solution. Additional components that may be present area reducing agent, such as DTT, primer molecules such as gene specific primers (GSP), random primers of any suitable length, oligo(dT) compounds of any suitable length, anchored oligo(dT) molecules of suitable length, detergents or mixtures of detergents such as Tween, NP-40, Big Chap, Chapso and equivalent reagents, dNTPs, and one or more RNase inhibitor proteins. The relative amounts contained in the mixture of such reagents necessary for use in RT-PCR reactions can be readily determined by the skilled artisan.

More specifically, the reagent mixture according to the present invention comprises a ready to use reagent solution that demonstrates prolonged stability when stored at −20° C., wherein the solution comprises (a) trehalose in a concentration between about 5% and about 35%, (b) a viral reverse transcriptase in a concentration sufficient for use in a reverse transcription reaction without adding additional reverse transcriptase, wherein said viral reverse transcriptase is selected from the group consisting of AMV RT, RSV RT, MMLV RT, HIV RT, EIAV RT, RAV2 RT, ASLV RT, and RNaseH (−) RT such as Superscript II RT and ThermoScript RT, and (c) one or more DNA polymerases selected from the group consisting of Taq, Tth, Tfi, Tbr, Tma, Tne, pfu, Pwo, Vent, Deep Vent, Kod, and mutants thereof, in a buffer suitable for use in a reverse transcription reaction, wherein the buffer comprises a co-factor metal ion necessary for reverse transcriptase activity and nucleoside triphosphates. Preferably, the concentration of trehalose may be between about 10% and about 35% for better stability of the mixture.

The buffer may further comprise at least one primer suitable for priming reverse transcription of a template by said reverse transcriptase. The buffer may further include an RNase inhibitor protein and/or bovine serum albumin. Moreover, the buffer may additionally include a potassium salt, a magnesium salt, nucleoside triphosphates, DTT, at least one or two primers suitable for priming reverse transcription of a template by said reverse transcriptase, at least one non-ionic detergent, and an RNase inhibitor protein. The solution of the present invention may further include an additional viral reverse transcriptase enzyme(s) and/or an additional DNA polymerase enzyme(s).

Besides, the buffer may further include at least one random primer (e.g. hexameric, heptameric, octameric, etc.) and/or at least one gene-specific primer. The buffer may include at least oligo dT primer (e.g. dT-6-10, dT-12-18). Alternatively, the buffer may include at least one random primer and at least one oligo dT. The metal ion necessary for reverse transcriptase and DNA polymerase activity may magnesium ion and the buffer may include a monovalent cation (e.g. K, Na). Moreover, the buffer may further comprise a reducing agent (e.g. DTT) and/or a non-ionic detergent (e.g. NP-40, Tween-20, Big Chap, Chapso). Furthermore, the solution of the present invention is stable for 1 month to 2 years when stored at −20° C.

Accordingly, the present invention provides newly improved, convenient, and ready to use configurations for RT-PCR. The methods of the invention reduce the number additions for assembly of RT-PCR reactions which is highly sought by researchers especially in high throughput applications.

According to the methods of the invention, the ready to use mixes for RT-PCR can be made at different concentrations and provided as 1× to 10× "mastermixes." The following is an example of a 2× mastermix for RT-PCR that contains all components necessary for RT-PCR according to the methods of this invention. Using 12.5 uL of this mastermix and RNA preparation of interest at a total volume of 25 uL provides a complete reaction mix for conversion and amplification of RNA molecules into cDNA.

Formulation for 2× RT-PCR Mastermix:
2× Buffer (80 mM Tris-HCl, pH 8.4, 0.2 M KCl),
3 mM MgCl$_2$ 0.4 mM dNTP (each),
10 nM oligo(dT)$_{20}$ 20 ng random hexamer,
19% Trehalose,
0.2% Chapso,
5 units of MMLV(RnaseH-) RT, and
2 units of Taq DNA polymerase.

In addition to the above formulation, three other mastermixes were prepared that contained all reagents except the primers.

RT-PCR Mastermix 1 did not have random primers.
RT-PCR Mastermix 2 did not have oligo dT primers.
RT-PCR Mastermix 3 did not have both random primer and oligo-dT.

All of the above 2× RT-PCR mastermixes were found to be stable for months when stored at −20° C. FIG. 3 shows the results and the efficacy of RT-PCR products with these mastermixes.

It will be evident to those skilled in the art that a variety of different reverse transcriptases can be used according to the method of the invention. The reverse transcriptases may include, without limitation, AMV RT, RSV RT, MMLV RT, RNase H-mutants of various reverse transcriptases, HIV RT, EIAV RT, RAV2 RT, TTH DNA polymerase, C. hydrogenoformans DNA polymerase, Superscript II RT, SuperScript RT, ThermoScript RT and mixtures thereof. It will also be obvious that one or more of the components of the above mastermix can be substituted with other equivalent reagent or protein. For example, there are a number of different RNase inhibitor proteins that can be used. Thermostable DNA polymerases suitable for use in the mastermixes are well known in the art and include Taq, Tth, Tne, Tma, Tli, Pfu, Pwo, Bst, Bca, Sac, Tac, Tfl, Tru, Mth, Mtb, and Mlep DNA polymerases and the like.

The composition of the 2× buffer provided can also be varied, for example, by use of other buffers such as sulfate containing buffers or acetate based buffers that have been used for RT-PCR. It will be apparent to those skilled in the art that different formulations can be optimized for different applications.

A variety of formulations have been described for One-step RT PCR, however, in all cases the buffers and enzymes are kept separately and are only mixed immediately prior to reverse transcription reaction. According to the methods of the invention, the reverse transcriptase, Taq DNA polymerase and buffers, dNTP's, co-factors and all other components for one step RT PCR can be mixed together in a variety of different concentrations to provide a ready to use mastermix.

EXAMPLES

FIG. 1: Freeze-Thaw Stability
Test samples were: (1) Control 1-Step RT-PCR (Legene), (2) SM-A: 1-Step RT-PCR Mastermix (2×, sample 1), and (3) SM-B: 1-Step RT-PCR Mastermix (2×, sample 2). Samples were subjected to number of freeze-thaw cycles as indicated (used dry-ice and room temperature thaw) and placed all samples on ice. Reactions were assembled by adding 10 pg of total HeLa RNA, and GAPDH-530 GSP primers and carried out incubation at 40° C. for 20 minutes RT reaction, heat-killed RT upon incubation at 85° C. for 5 minutes, then followed by 40 cycles of PCR amplification (94° C., 15 s, 60° C., 30 s, 72° C., 1 min) and analyzed the RT-PCR product by 1% agarose gel electrophoresis.

FIG. 2: Real Time Storage Stability
5 months old samples were removed from −20° C. freezer. (1) 1-Step RT-PCR Mix-A (2×, MMLV RT), (2) 1-Step RT-PCR Mix-B (2×, MMLV RT), (3) 1-Step RT-PCR Mix-C (5×, MMLV RT), (4) 1-Step RT-PCR Mix-A (5×, MMLV RT), (5) Control 1-Step RT-PCR (Legene), (6) 1-Step RT-PCR Mix-E (2×, RnaUsScript-20 RT), and (7) 1-Step RT-PCR Mix-F (5×, RnaUsScript-20 RT). SM-A: 1-Step RT-PCR Mastermix (2×, sample 1), (3). SM-B: 1-Step RT-PCR Mastermix (2×, sample 2). Reactions were assembled by adding 10 ng of total HeLa RNA, and Htf-1000 bp GSP primers and carried out incubation at 40° C. for 20 minutes RT reaction, heat-killed RT upon incubation at 85° C. for 5 minutes, then followed by 40 cycles of PCR amplification (94° C., 15 s, 60° C., 30 s, 72° C., 1 min) and analyzed the RT-PCR product by 1% agarose gel electrophoresis.

FIG. 3: 1-Step RT-PCR with 2× and 5× RT-PCR Mastermixes

Test samples were: (1) Control 1-Step RT-PCR (Legene), (2) 1-Step RT-PCR Mastermix (2×, sample 1), and (3) 1-Step RT-PCR Mastermix (5×, sample 2). Reactions were assembled by adding 10 ng of total HeLa RNA, and Htf-610 bp, Htf-1000 bp, Hrpa-1092 bp, and Hp2a-1093 bp primers as indicated and carried out incubation at 40° C. for 20 minutes RT reaction, heat-killed RT upon incubation at 85° C. for 5 minutes, then followed by 40 cycles of PCR amplification (94° C., 15 s, 60° C., 30 s, 72° C., 1 min) and analyzed the RT-PCR product by 1% agarose gel electrophoresis.

According to the tests, the 2× and 5× cDNA synthesis mastermixes were found to be stable for more than 7 months when stored at −20 C.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. A reagent mixture comprising a ready to use reagent solution, wherein the solution comprises:
   (a) trehalose in a concentration between 7% and 22%;
   (b) a viral reverse transcriptase in a concentration sufficient for use in a reverse transcription reaction without adding additional reverse transcriptase, wherein the viral reverse transcriptase is selected from the group consisting of Avian Myeloblastosis Virus Reverse Transcriptase, Respiratory Syncytial Virus Reverse Transcriptase, Moloney Murine Leukemia Virus Reverse Transcriptase, Human Immunodeficiency Virus Reverse Transcriptase, Equine Infectious Anemia Virus Reverse Transcriptase, Rous-Associated Virus 2 Reverse Transcriptase, Avian Sarcoma Leukosis Virus Reverse Transcriptase, RNaseH (−) Reverse Transcriptase, SuperScript II Reverse Transcriptase, and ThermoScript Reverse Transcriptase; and
   (c) at least one DNA polymerases selected from the group consisting of Thermus Aquaticus, Thermus Thermophilus, Thermus Filiformis, Thermus Brockianus, Thermus Phage, Thermotogo Neapolitana, Pyrococcus Furiosus, Pyrococcus Woesei, Vent, Deep Vent, Kodakaraensis, and mutants thereof; and
   (d) at least one random primer or at least one oligo deoxythymine primer or both random primer and oligo-thymine primer,
   in a buffer suitable for use in a reverse transcription reaction, wherein the buffer comprises:
   a co-factor metal ion necessary for reverse transcriptase activity; and
   nucleoside triphosphates.

2. The mixture according to claim 1, wherein the buffer further comprises at least one additional primer suitable for priming reverse transcription of a template by the reverse transcriptase.

3. The mixture according to claim 1, wherein the buffer comprises an RNase inhibitor protein.

4. The mixture according to claim 1, wherein the buffer comprises bovine serum albumin.

5. The mixture according to claim 1, wherein the buffer comprises a potassium salt, a magnesium salt, nucleoside triphosphates, Dithiothreitol, at least one primer suitable for priming reverse transcription of a template by the reverse transcriptase, at least one non-ionic detergent, and an RNase inhibitor protein.

6. The mixture according to claim 1, wherein the solution comprises at least two viral reverse transcriptase enzymes.

7. The mixture according to claim 1, wherein the solution comprises at least two DNA polymerase enzymes.

8. The mixture according to claim 1, wherein the buffer further comprises hexameric oligonucleotides, heptameric oligonucleotides, or octameric oligonucleotides.

9. The mixture according to claim 1, wherein the buffer comprises at least one gene-specific primer.

10. The mixture according to claim 1, wherein the buffer comprises deoxy-thymine-6-10 or deoxy-thymine-12-18.

11. The mixture according to claim 1, wherein the metal ion necessary for reverse transcriptase activity is magnesium ion.

12. The mixture according to claim 1, wherein the buffer comprises a monovalent cation.

13. The mixture according to claim 1, wherein the buffer comprises K or Na.

14. The mixture according to claim 1, wherein the buffer comprises a reducing agent.

15. The mixture according to claim 1, wherein the buffer comprises Dithiothreitol.

16. The mixture according to claim 1, wherein the buffer comprises a non-ionic detergent.

17. The mixture according to claim 1, wherein the buffer comprises non-ionic or zwitterionic detergent.

18. The mixture according to claim 1, wherein the solution is stable for 1 month to 2 years when stored at −20° C.

* * * * *